United States Patent [19]

Paulson, Jr.

[11] Patent Number: 5,408,321
[45] Date of Patent: Apr. 18, 1995

[54] APPARATUS FOR MEASUREMENT OF SPECIFIC DICHROISM OF SHEET MATERIALS

[75] Inventor: Charles M. Paulson, Jr., Hockessin, Del.

[73] Assignee: E. I. Du Pont de Nemours and Company, Wilmington, Del.

[21] Appl. No.: 71,890

[22] Filed: Jun. 7, 1993

[51] Int. Cl.[6] .......................... G01J 4/00; G01N 21/84
[52] U.S. Cl. ..................................... 356/366; 356/431; 250/225
[58] Field of Search ............... 356/366, 367, 370, 429, 356/430, 431; 250/225

[56] References Cited

U.S. PATENT DOCUMENTS

| 3,345,907 | 6/1963 | Wada | 88/14 |
| 4,019,819 | 4/1977 | Lodzinski | 356/431 |
| 4,309,110 | 1/1982 | Tumerman | 356/365 |
| 4,521,111 | 6/1985 | Paulson, Jr. et al. | 356/367 |
| 4,631,408 | 12/1986 | Zelmanovic et al. | 250/339 |

OTHER PUBLICATIONS

A. Wada and S. Kozawaya, "Instrument For The Studies Of Differential Flow Dichroism Of Polymer Solutions", Journal Of Polymer Science: Part A, vol. 2, pp. 853 to 864 (1964).

Primary Examiner—Robert P. Limanek
Assistant Examiner—David B. Hardy

[57] ABSTRACT

An apparatus for providing signals representative of angle of maximum absorbance $\theta_{max}$, specific dichroism ($\Delta A/A$), and absorbance A of a sheet of light absorbing sheet material is disclosed.

13 Claims, 8 Drawing Sheets

APPARATUS FOR MEASUREMENT OF SPECIFIC DICHROISM OF SHEET MATERIALS

FIELD OF THE INVENTION

The present invention generally relates to the detection of optical characteristics of sheet materials, more particularly to detecting absorption characteristics of sheet materials by polarization measurement methods, and most particularly to simultaneously detecting three optical characteristics of an optically absorbing sheet material at one or more predetermined wavelengths specific dichroism, the angle of maximum absorbance, and the average absorbance.

DESCRIPTION OF THE RELATED ART

In the manufacture of molecularly oriented polymeric films and sheet materials, certain properties of the film, such as modulus and coefficient of thermal expansion, are related to the molecular orientation of the polymer. In a typical sheet manufacturing process both the direction and extent of polymer chain orientation vary across the transverse direction (TD) width of the film, while the orientation properties remain reasonably constant in the machine direction (MD). Variation of properties across the width of film is undesirable for many end use applications of the film. Therefore, measurement of uniformity of molecular orientation is important to fully characterize the film and to provide information for controlling the manufacturing process to make a more uniform product. Measurement of this molecular orientation has traditionally been done by labor intensive laboratory methods and results are generally not available in a sufficiently short time to be useful for effective control of the manufacturing process.

Films in which the molecular chains are oriented are known to absorb plane-polarized light differently at different angles of polarization. This variation of absorbance property is known as "dichroism". The measurement of dichroism, using an intermittent source of monochromatic light having two discrete, alternating polarization vectors is disclosed in U.S. Pat. No. 3,345,907 (Wada). The requirement for the user to adjust manually the orthogonal polarizers to the angle which produces the maximum dichroic effect and the intermittent nature of the measurement makes this technique time-consuming in the laboratory and impractical for on-line measurement of a moving sample.

The measurement of dichroism using a source of monochromatic light having a rotating polarization vector is taught by U.S. Pat. No. 4,309,119 (Turnerman). This method, while an improvement over the method above-described, suffers from several disadvantages which reduce its utility for manufacturing operations. The latter method, while able to measure a transmission parameter related to dichroism, is not capable of simultaneously determining the dichroism, the angle of maximum absorbance, and the average absorbance. Both of these methods are therefore believed not particularly useful for on-line application in the manufacture of molecularly oriented polymeric films, where both the direction and magnitude of the molecular orientation may vary continuously across the transverse direction width of the film.

Another technique for the measurement of molecular orientation of polymeric material detects the intensity of fluorescent radiation emitted when the material is excited by polarized light. This technique is disclosed in U.S. Pat. No. 4,521,111 (Paulson and Faulhaber). This technique is only useful for measuring properties of materials that fluoresce when excited by ultraviolet radiation.

SUMMARY OF THE INVENTION

The present invention relates to an apparatus for detecting polarization dependent properties of a light absorbing sheet material having an absorbance characteristic A, an absorbance variation due to polarization $\Delta A$, and a reflection loss factor F. The apparatus comprises an illuminator, a light receiver, a first reference signal generator, a second reference signal generator, and an analysis circuit for generating signals representative of specific dichroism, angle of maximum absorbance, and average absorbance of the sheet. The illuminator and the receiver define an optical path.

The illuminator illuminates a sheet of light absorbing sheet material with a beam of unpolarized light. The light receiver, which includes a rotating polarization filter, receives light transmitted through the sheet and generates a sinusoidally varying light intensity signal $I_s$ representative of the intensity of polarized light in a predetermined range of wavelengths. The intensity signal $I_s$ has a minimum value $I_{s\ rain}$ at a first polarization angle of maximum absorbance $\theta_{max}$ and a maximum value $I_{s\ max}$ at a second polarization angle of minimum absorbance $\theta_{min}$. The first reference signal generator generates a first reference signal $I_\theta$ representative of the polarization angle $\theta$ of the rotating polarization filter. The second reference signal generator generates a second reference signal $F.I_0$ representative of the intensity of the beam of unpolarized light from the illuminator scaled by the reflection loss factor F.

The analysis circuit is responsive to the light intensity signal $I_s$, the first reference signal $I_\theta$, and the second reference signal $F.I_0$ to generate signals representative of angle of maximum absorbance $\theta_{max}$,
specific dichroism $(\Delta A/A)$, and
absorbance A of the sheet.
where specific dichroism $(\Delta A/A)$ is defined as:

$$(\Delta A/A) = \frac{\log I_{s\ min} - \log I_{s\ max}}{\log F \cdot I_0 - 1/2\ I_{s\ min} - 1/2 \log I_{s\ max}};$$

and the absorbance A is defined as $$A = \log F.I_0 - \tfrac{1}{2} \log I_s \text{rain} - \tfrac{1}{2} \log I_{s\ max}$$

BRIEF DESCRIPTION OF THE DRAWINGS

The invention will be more clearly understood from the following detailed description, in which.

DETAILED DESCRIPTION OF THE INVENTION

Throughout the following detailed description, similar reference numerals refer to similar elements in all Figures of the drawings.

Principle of Measurement

The apparatus of the present invention measures, preferably in a simultaneous manner, various characteristics of a sheet material. These characteristics are: (1) a quantity referred to and defined hereinafter as "specific dichroism"; (2) the angle of maximum absorbance; and (3) the absorbance at selected wavelengths for an optically anisotropic light absorbing sheet material, such as a polymeric film. An example of an anisotropic polymeric film the polarization dependent properties of which are measurable using the apparatus of the present invention is poly-[N,N'-bis(phenoxyphenyl)-pyromellitimide], commonly referred to as "PMDA-ODA polyimide". Exemplary of a polyimide film which is optically absorbing in the visible wavelength range is that manufactured and sold by E. I. du Pont de Nemours and Company under the trade, mark KAPTON ®. A typical wavelength range of four hundred sixty to five hundred forty (460 to 540) nanometers (nm) has been found to be appropriate for measuring the above-mentioned three parameters for polyimide film. Other visible wavelength ranges and non-visible wavelength ranges, such as infrared or ultraviolet, may also be utilized, depending on the spectral absorbance characteristics of the sheet material to be characterized.

Figure 1A:
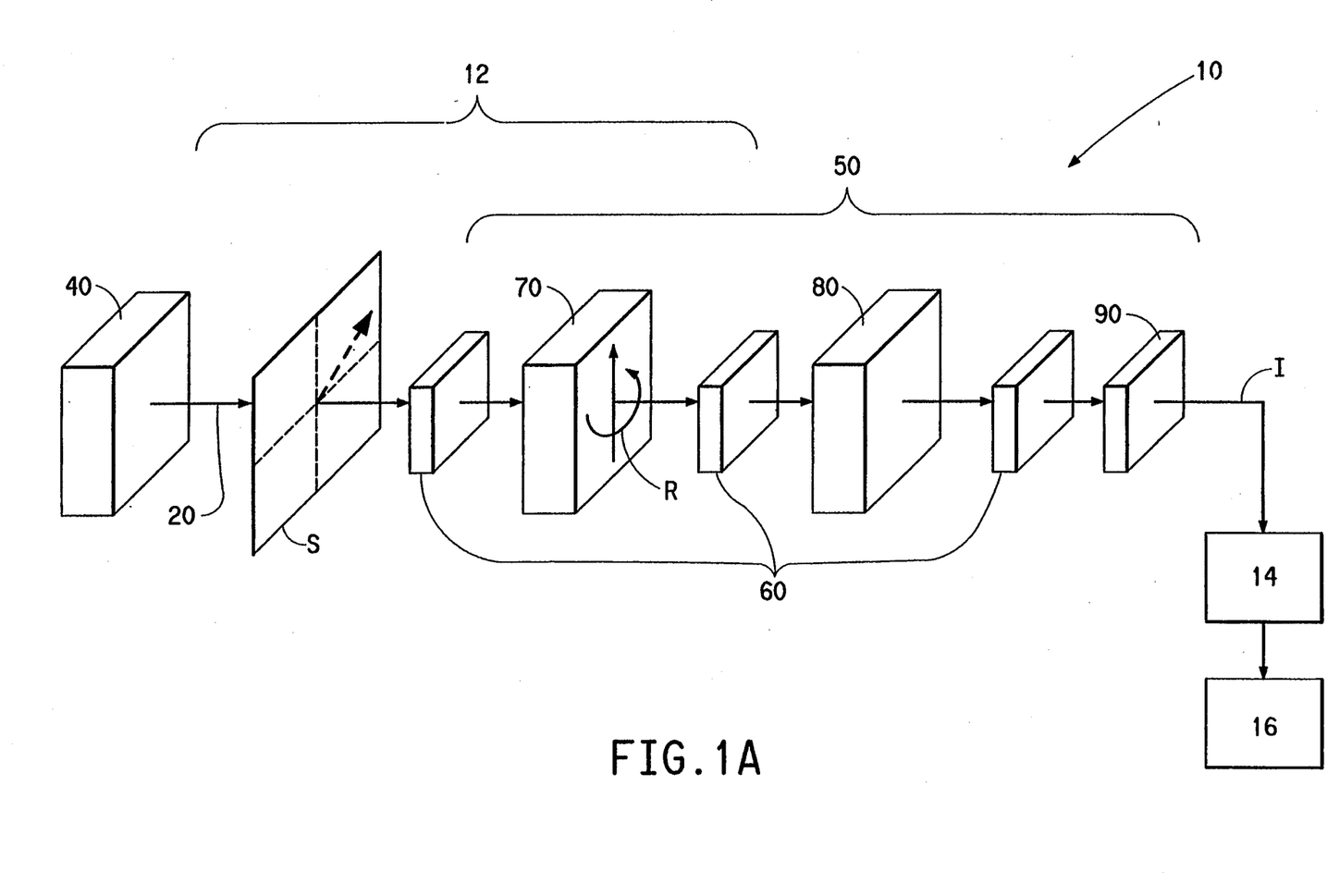
FIG. 1A is a schematic diagram of the apparatus of the present invention illustrating the measurement principle implemented thereby.
Figure 3:
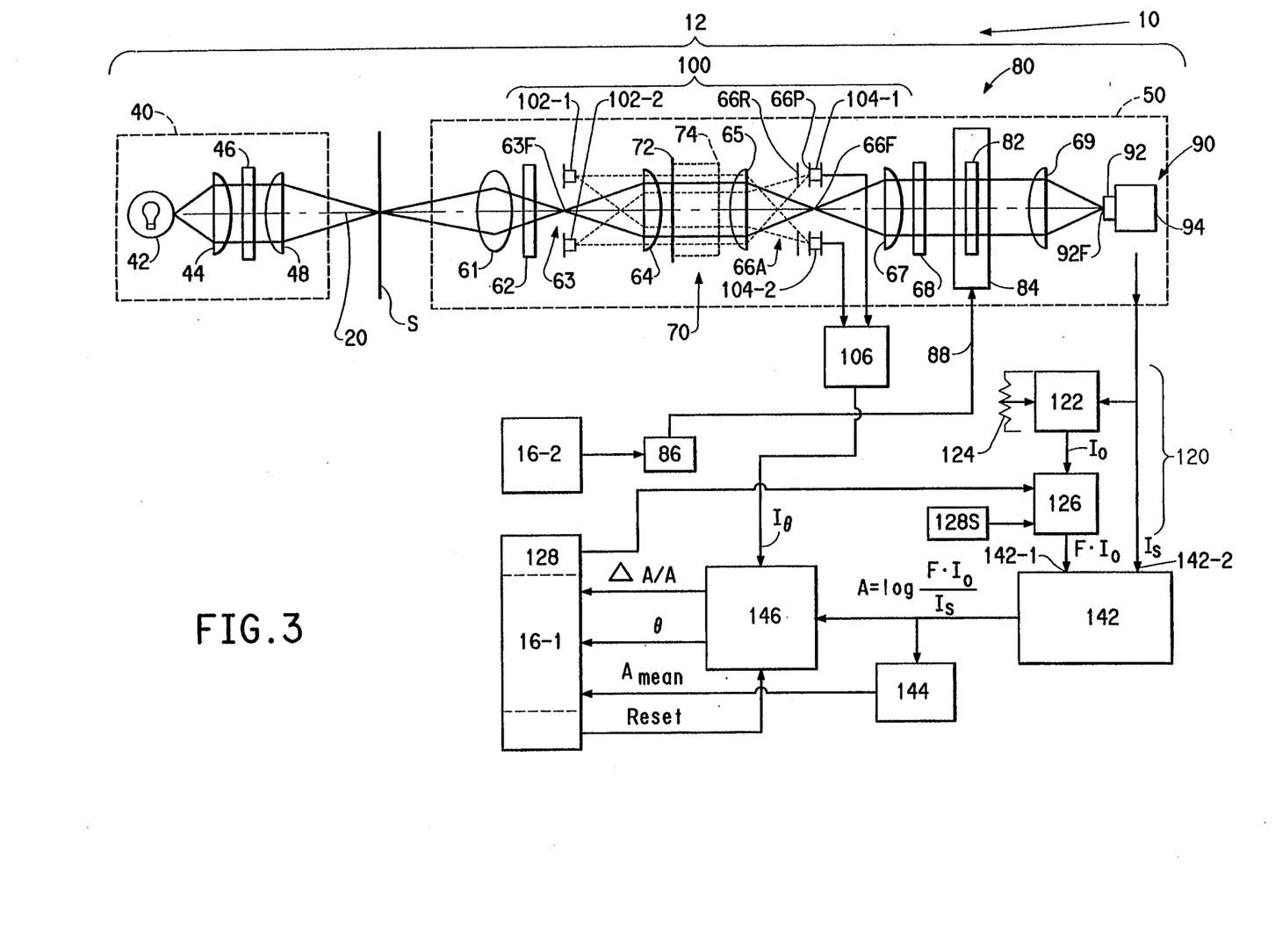
FIG. 3 is a schematic diagram of the optical subsystem and signal analysis circuit of the apparatus of FIG. 2.
Figure 4:
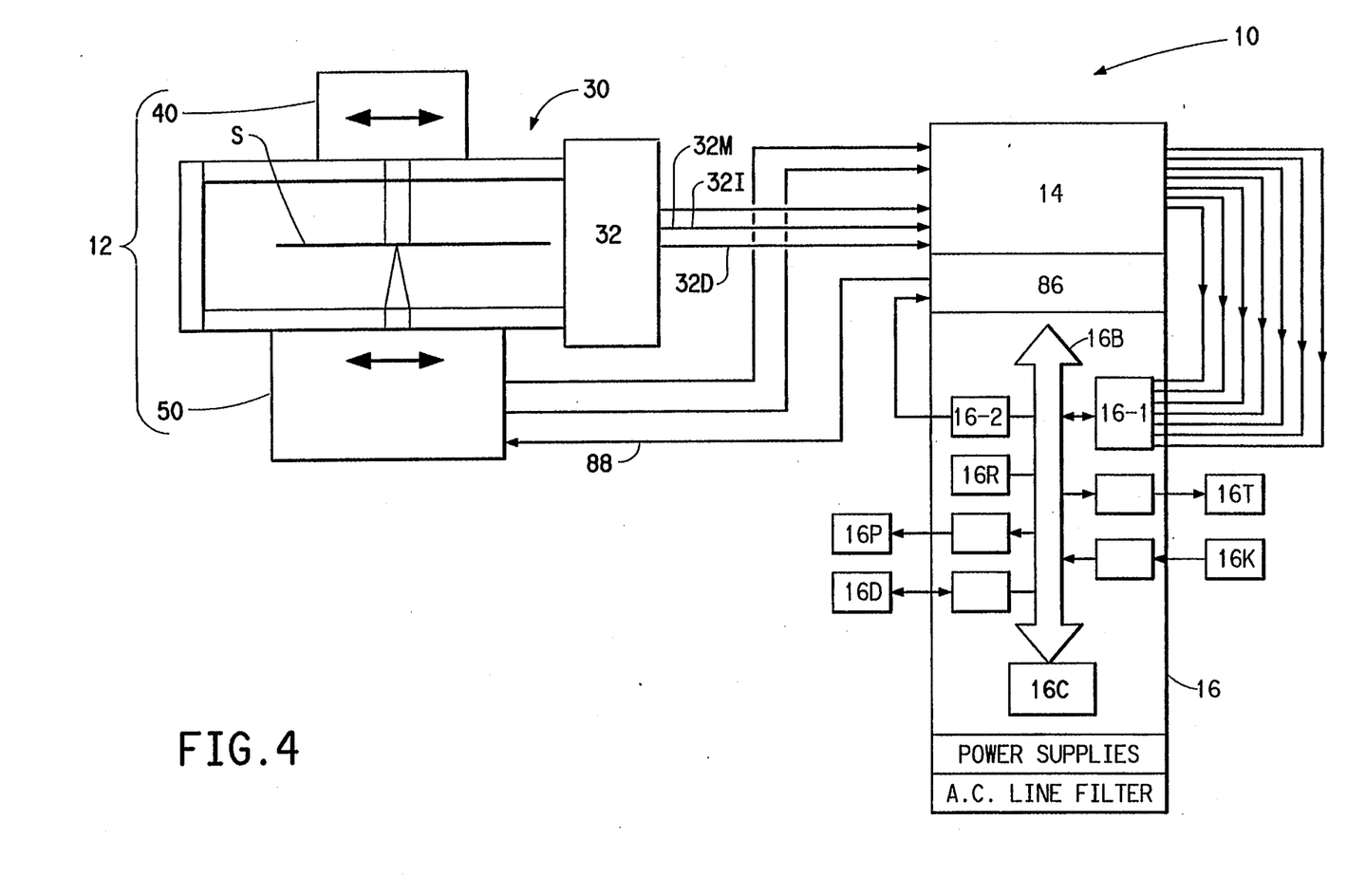
FIG. 4 is a sectional view and block diagram of an apparatus in accordance with a second embodiment the present invention.
Figure 5:
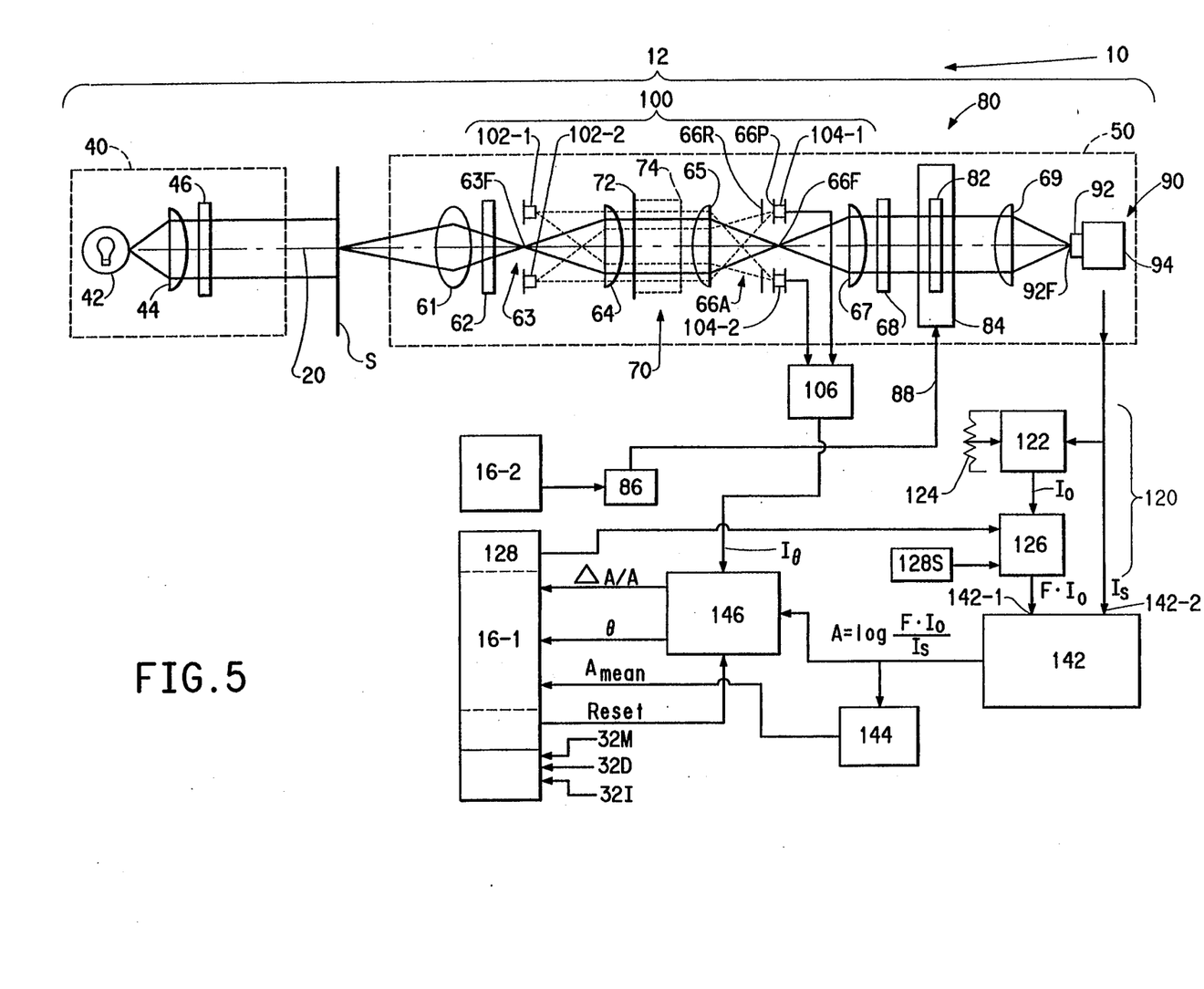
FIG. 5 is a schematic diagram of the optical subsystem and signal analysis circuit of the apparatus of FIG. 4.

As will be fully developed herein, the apparatus 10 of the present invention comprises three subsystems: an optical subsystem 12, a signal analysis subsystem 14 and a control and recording subsystem 16. The diagram in FIG. 1A is a schematic diagram illustrating the principle of the measurement implemented by the optical subsystem 12. The optical subsystem 12 includes an illuminator generally indicated by the reference character 40 and a light receiver generally indicated by the reference character 50. An optical path 20 is defined by the illuminator 40 and the light receiver 50. A beam of unpolarized light from the illuminator 40 passes through a sheet of optically anisotropic light absorbing sheet material (or film) indicated by the reference ,character S placed in the optical path 20 to the light receiver 50. Depending upon the embodiment of the invention the beam of unpolarized light propagating along the optical path 20 may be either focussed (FIG. 2 and 3) or collimated (FIGS. 4 and 5). The light receiver 50 includes an optics assembly 60, a polarization filter assembly 70, an optical pass band filter assembly 80, and a photodetector detector assembly 90. The polarization filter assembly 70 includes a polarization filter that rapidly rotates in a direction indicated by the arrow R. The electrical signal I output from the photodetector detector assembly 90 is representative of the intensity of the polarized light reaching the photodetector assembly 90. This intensity signal I is applied to the analysis subsystem 14. The results of the analysis are recorded by the control and recording subsystem 16. The electrical signal I is designated $I_s$ when sheet material S is present in the optical path 20, and is designated $I_0$ when sheet material S is absent therefrom. A suitable sheet presence detector is provided as will be discussed herein.

Figure 1B:
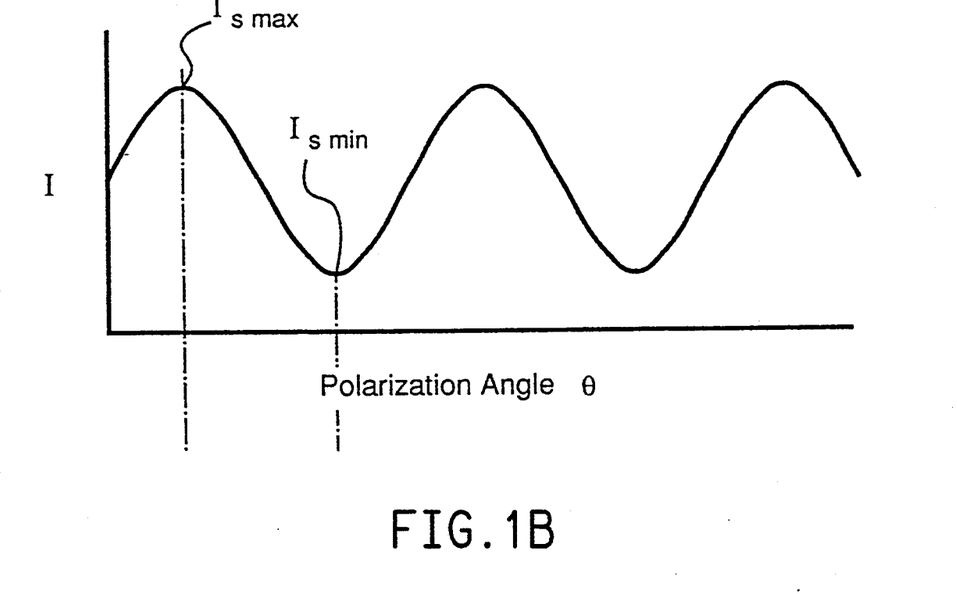
FIGS. 1B and 1C are plots which respectively illustrate the light intensity $I_s$ and the absorbance A, both as a function of polarization angle $\theta$.
Figure 1C:
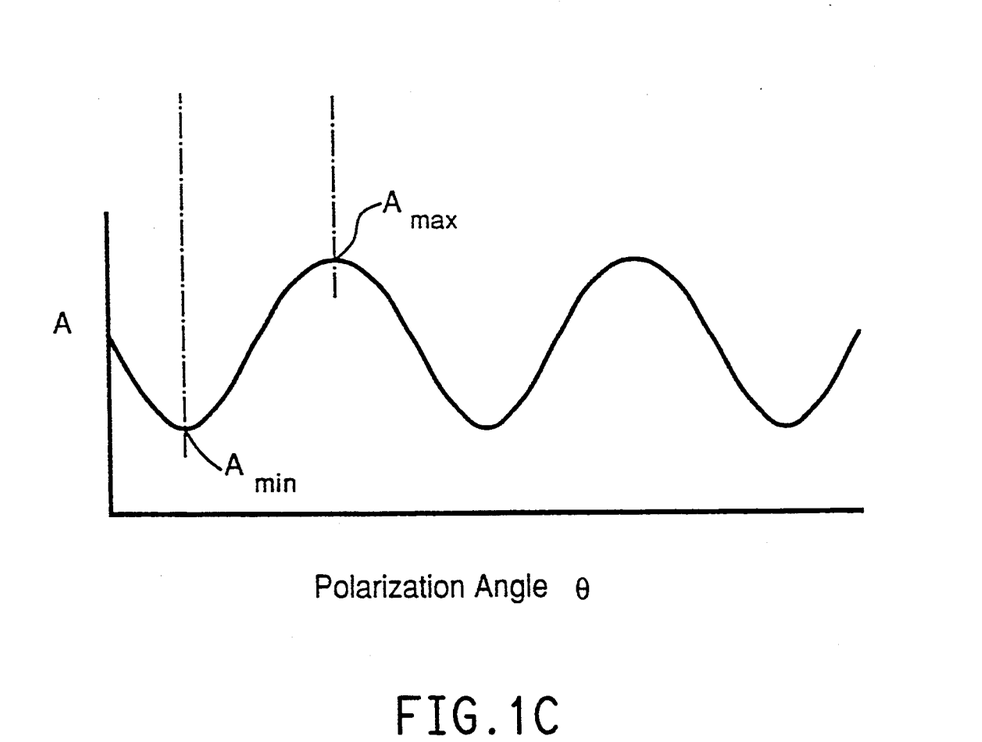

If the sheet material S has a preferred axis of absorption P (i.e., if the sheet material S is dichroic), then the photodetector assembly 90 produces an electrical signal $I_s$ sinusoidally varying in amplitude with a frequency twice that of the rotating filter within the polarization filter assembly 70. From FIGS. 1B and 1C it may be seen that the minimum signal amplitude $I_{s\ min}$ occurs when the angle of the polarization filter aligns with the preferred axis of absorption P to produce the maximum absorbance value $\theta_{max}$ of the sheet material. This angle of the polarization filter is indicated by the character $\theta_{max}$. The absorbance A of the sheet material is defined as $A = \log(F \cdot I_0/I_s)$, where $I_0$ is the electrical signal produced by the photodetector assembly 90 without the sheet material present in the optical path 20, $I_s$ is the electrical signal produced by the photodetector assembly 90 with the sheet material present in the optical path 20, and F is a factor which takes into account reflection losses in the sheet material S.

Figure 1D:
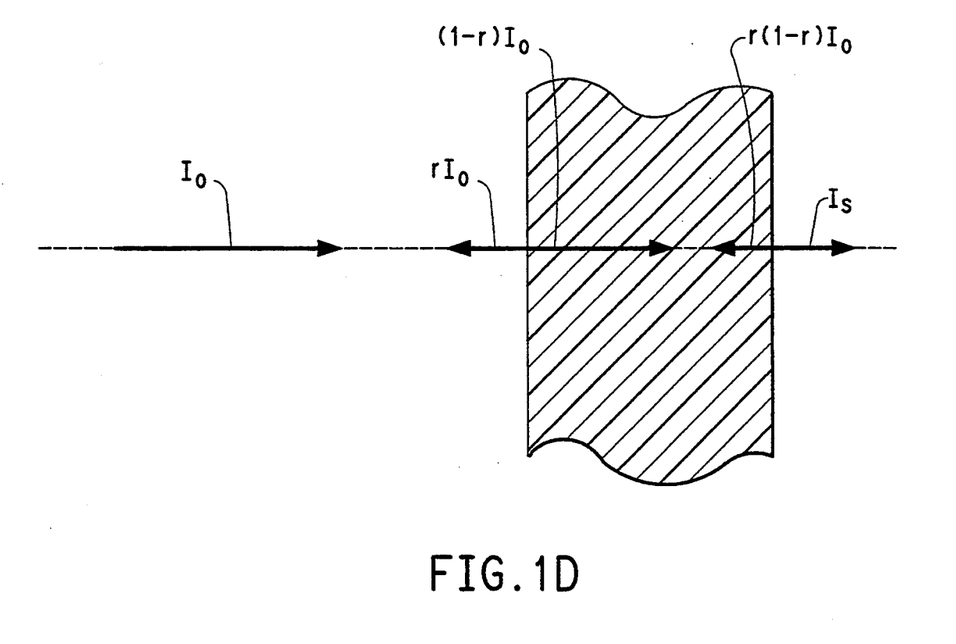
FIG. 1D is a schematic diagram which illustrates the mechanisms of reflection loss when light is transmitted through a sheet material.

Referring to FIG. 1D, light losses from the sheet material S are due to true absorption, scattering, and reflections. The following derivation provides a correction for first pass reflection losses from both sides of the sheet material under the assumptions of normal incidence, no polarization effects, homogeneous sheet material and multiple internal refections being negligible (true for highly absorbing sheet materials). From FIG. 1D, the light intensity $I_s$ emerging from the sheet material is given by $$I_s = (I_0 - I_0 \cdot r)e^{-\alpha x} - r(I_0 - I_0 \cdot r)e^{-\alpha x}$$

where r is the fractional reflectance at the interface and $\alpha$ is the attenuation per distance $\Delta x$ in the film. Therefore, $$I_s = I_0 (1 - r)^2 e^{-\alpha x} \text{ and}$$

$$\log \frac{I_0 (1 - r)^2}{I_s} = \frac{\alpha x}{2.303} = A$$

From the Fresnel relationships, $$r = \left(\frac{n - 1}{n + 1}\right)^2$$

See, generally, K. J. Clevett, *Process Analyzer Technology*, John Wiley & Sons, 1986.

A film such as PMDA-ODA (KAPTON ® film) has an average refractive index $n = 1.75$; therefore the fractional reflectance $r = 0.0744$ and the factor $F = (1 - r)^2 = 0.8567$.

The polarization dependent change in optical absorbance is known as "dichroism" $\Delta A$. Dichroism is defined as $$\Delta A = A_{max} - A_{min}$$

where $A_{max}$ and $A_{min}$ are the maximum and minimum absorbances, respectively, (i.e., with the polarizer vector respectively parallel and perpendicular to the preferred axis of absorption P of the sheet material). "Specific dichroism," the ratio $(\Delta A/A)$, is defined with relation to the absorbance A in the plane of the sheet material as $$(\Delta A/A) = \frac{(A_{max} - A_{min})}{0.5(A_{max} + A_{min})} = \frac{2(A_{max} - A_{min})}{(A_{max} + A_{min})}$$

The parameter specific dichroism is a measure of the orientation unbalance in the plane of the sheet material and can vary from zero for a completely isotropic distribution of absorption axes to 2.0 for complete alignment of absorption axes in one direction in the plane of the sheet material. The relationship $(\Delta A/A)$ to polymer chain axis orientation depends upon the direction of the absorption axis with respect to the chain axis, so $(\Delta A/A)$ may be less than 2.0, even for complete alignment of rigid polymers. For low values of $(\Delta A/A)$, the absorbance A is inversely proportional to $I_s$ and $(\Delta A/A) = AC/DC$, where AC is the peak-to-peak alternating component of the absorbance A and DC is the local average or local mean level of the absorbance A. The angle of maximum absorbance $\theta_{max}$ is determined from the phase of the absorbance A with respect to a reference waveform that has a known phase relationship to a predetermined direction in the sheet material. The direction is usually defined in terms of the longitudinal axis of the manufacturing machinery, also known as "machine direction" (MD) of the sheet material.

Another often calculated orientation parameter is the dichroic ratio R, defined as $$R = A_{max}/A_{min}$$

Therefore, specific dichroism $(\Delta A/A) = 2(R-1)/(R+1)$.
For small values (i.e., <0.3) of specific dichroism $(\Delta A/A)$ $$R \approx e^{(\Delta A/A)} \approx 1 + (\Delta A/A)$$

Figure 2:
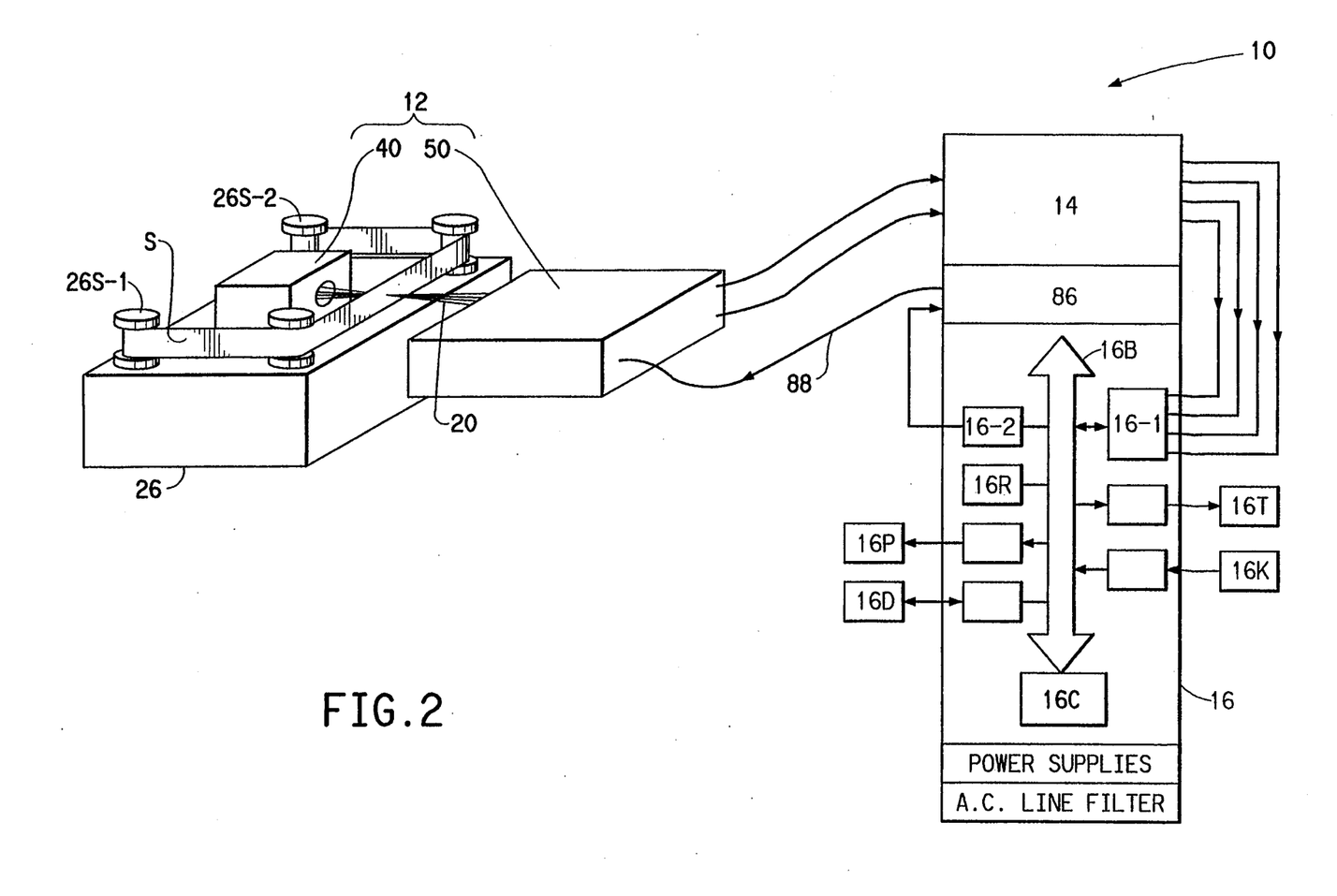
FIG. 2 is a stylized pictorial representation and block diagram of an apparatus in accordance with a first embodiment the present invention.
Figure 6:
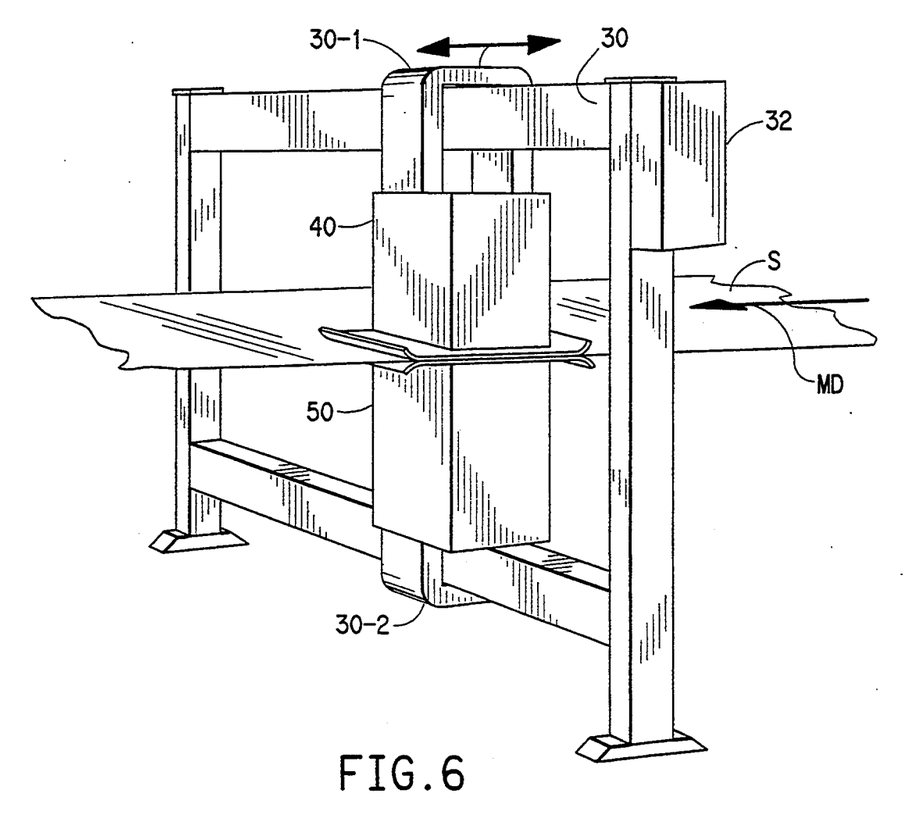
FIG. 6 is a stylized pictorial representation of the optical subsystem of FIG. 5 mounted on a traversing transport unit.

As noted, the apparatus 10 of the present invention comprises the optical subsystem 12, the signal analysis subsystem 14, and the control and recording subsystem 16. There are two embodiments of the present invention, each having a particular preferred utility. A first embodiment, seen in FIG. 2 and 3, is especially suited for laboratory (off-line) use, while a second embodiment, seen in FIGS. 4 through 6, is especially suited for automatic measurement of the optical characteristics of a moving web of sheet material, such as during the manufacture of that material (on-line use).

In the first embodiment (FIG. 2) the optical subsystem 12 is fixed in relation to the sheet material S whose optical characteristics are being measured and utilizes a focussed beam of unpolarized light. The sheet material S is spooled past the optical subsystem 12 by a drive unit 26. The optical subsystem 12 is rigidly mounted to the drive unit 26. In the second embodiment (FIG. 4) the optical subsystem 12 utilizes a collimated beam of unpolarized light and further includes a traversing transport unit 30 (in place of the drive unit 26) that positions the optical subsystem 12 relative to a moving web of sheet material S. The transport unit 30 traverses the optical subsystem 12 across the moving web of sheet material S to continuously measure the transverse profile of the polarization dependent optical characteristics of the sheet material as it is being manufactured.

In both embodiments the signal analysis is subsystem 14 and the control and recording subsystem 16 (as well as associated power supplies) are housed in a suitable enclosure, such as a standard rack mount cabinet. To insure compatibility of the system to industrial environments, AC power to all components is supplied by a AC line filter, such as a Model LCR-2400 available from Tripp-Lite Corporation, Chicago, Ill. which provides both voltage regulation capability and circuit breaker protection.

Description of First Embodiment

FIGS. 2 and 3 show the first embodiment of the invention. Suitable for use as the drive unit 26 is a Mekel 70 mm film transport available from Mekel Engineering Inc. Walnut, Calif.

A more detailed diagram of the optical subsystem 12 and the control and signal analysis subsystem 14 of the first embodiment of the present invention is shown in FIG. 3.

The illuminator 40 illuminates the sheet material S in the optical path 20. The illuminator 40 includes a suitable light source 42, such as a twenty (20) watt halogen lamp, typically a model L9404 available from Gillway Corporation, Woburn, Mass. The light from the source 42 is collimated by a first lens 44, such as a twenty-five (25) millimeter focal length Model KPX076 lens, directed through a quartz wedge-type depolarizer plate 46 such as a model DPU-25 available from Optics for Research, Caldwell, N.J. The axis of the depolarizer plate 46 is adjusted so that the partially polarized light emitted from the lamp filament of the light source 42 is depolarized. The combination of the light source 42, the first lens 44, and the depolarizer plate 46 thus comprises a source of unpolarized light. The unpolarized light emerging from the depolarizer plate 46 is focused to a focal point or spot on the sheet material S by a second lens 48, such as a sixty-three (63) millimeter focal length Model KPX133 lens. This lens comprises focussing means for receiving light from the source and forming a beam focussed to a focal point on the sheet material.

The light receiver 50 receives light transmitted through and emerging from the sheet material S. The light receiver 50 comprises the optics assembly 60, the polarization filter assembly 70, the passband assembly 80 and the photodetector assembly 90. (Elements of each assembly are indicated in the drawings and the discussion by reference characters within the same decade.) Arranged in optical sequence the light receiver 50 includes a first focussing lens 61, a filter 62, an aperture plate 63, a first collimating lens 64, the rotating polarization filter assembly 70, a second focussing lens 65, a multifunctional aperture assembly 66, a second collimating lens 67, a depolarizer plate 68, the narrow wavelength passband filter assembly 80, a third focussing lens 69, and the photodetector assembly 90. Lenses found suitable for the optical subsystem 12 used in both embodiments of the present invention are those available from Newport Corporation, Fountain Valley, Calif., each having an anti-reflection coating, designated by the part number suffix +AR.14.

The first focussing lens 61, such as a fifty (50) millimeter focal length Model KBX094 lens, focuses the received light to a first focal point 63F located in the center of the three (3) millimeter diameter first aperture 63. Light from the first lens 61 typically passes through the filter 62, which passes wavelengths used in the measurement of the desired optical properties and eliminates wavelengths which might interfere with generation of the first reference signal, as will be discussed below. In the illustrated example the filter 62 may be a Corning 9782 blue-green glass filter, to eliminate red wavelengths which might interfere with generation of the first reference signal. Light passing through the first aperture 63 is collimated by the first collimating lens 64, such as a fifty (50) millimeter focal length Model KPX082 lens. The first collimating lens 64 thus forms a first collimated beam. The rotating linear polarization filter assembly 70 includes a polarization filter 72, preferably an HNP'B Polaroid filter available from Polaroid Corporation, Norwood, Mass. The filter 72 is mounted on a hollow shaft motor 74, such as a Model M271026 sold by Vickers-Welco, Cincinnati, Ohio. The motor 74 typically rotates the filter 72 at thirty thousand (30,000) RPM. The filter 72 is positioned to receive the first collimated beam and to pass therethrough only the portion of the light in the first collimated beam whose polarization angle is aligned with the polarization angle of the filter 72.

The collimated beam emerging from the rotating polarization filter assembly 70 is focused by the second focussing lens 65, such as a fifty (50) millimeter focal length Model KPX082 lens, and directed toward a focal point 66F located at the center of the central aperture 66A of the multifunctional aperture assembly 66. The aperture assembly 66 includes an annular-shaped passband filter 66R sandwiched together with an annular fixed polarization filter 66P. (These latter elements are discussed herein in conjunction with a first reference signal generator).

Light passing through the aperture 66A is then collimated by the second collimating lens 67, such as a fifty (50) millimeter focal length Model KPX082 lens to form a second collimated beam. The second collimated beam passes through the depolarizer plate 68, such as a model DPU-25. The depolarizer plate 68 minimizes the effect of any polarization sensitivity arising from the subsequent wavelength passband filter assembly 80 or the photodetector assembly 90.

The passband filter assembly 80 includes a narrow passband filter element 82 positioned to receive the second collimated beam and pass therethrough only a predetermined range of wavelengths. A ten (10) nm bandwidth interference filter having a center wavelength of four hundred ninety (490) nanometers is typical. For convenience in practice, the passband filter assembly 80 is implemented using a filter wheel 84 such as that sold as Model 53855 by Oriel Corporation, Stratford, Conn., with a corresponding controller 86 sold by the same manufacturer as Model 77374. The wheel 84 carries a plurality of narrow passband filter elements 82, each suitable for a particular sheet material. The controller 86 positions a selected filter element 82 on the wheel 84 into the optical path in response to suitable control signals applied on a line 88.

Light emerging from the narrow passband filter 82 is then focused by a third focussing lens 69. The focussed light is directed toward the photodetector assembly 90 that generates the light intensity signal $I_s$. The photodetector assembly 90 includes a photodetector element 92 and associated amplifier 94. The focal point 92F of the third focussing lens 69 lies at the center of the photodetector element 92. Suitable for use as photodetector assembly 90 is a Model G1957 Gallium Arsenide Phosphide (GaAsP) photodiode/operational amplifier solid state detector device sold by Hammamatsu Corp., Bridgewater, N.J.

A first reference signal generator generally indicated by the reference character 100 is used to generate a fixed phase reference signal $I_\theta$ representative of the polarization angle $\theta$ of the rotating polarization filter 72. The first reference signal generator 100 comprises: a circular array of light emitting diodes 102 symmetrically disposed about the first focal point 63F which generate a plurality of reference beams; the annular fixed polarization filter 66P positioned adjacent the second focal point 66F; a circular array of photodetectors 104 symmetrically disposed about the second focal point 66F immediately behind the fixed polarization filter 66P; and a summing amplifier 106 each of whose inputs; is connected to a respective one of the photodetectors 104.

In the illustrated example one or more, preferably three, red light emitting diodes (LED's) 102-1, 102-2, 102-3 are arranged symmetrically around the first aperture 63. The light emitting diodes are typically are those sold by Gilway Corporation as Model E100. Light from each of the three red LED's is collimated by the first collimating lens 64 to form a reference beam. Each reference beam passes through the rotating polarization filter assembly 70, through the annular (red) passband filter 66R, through the annular fixed polarizer 66P and is focused by the second focussing lens 65 onto its respective photodiode 104-1, 104-2, 104-3 which converts the incident light intensity to an electrical signal. The photodetectors are typically photodiodes such as those sold by EG&G Vatec, St. Louis, Miss., as Model VTB1113. The annular passband filter 66F may typically be one available from Edmond Scientific, Barrington, N.J., and has a one-half transmission point $(T_{\frac{1}{2}})$ at a wavelength of five hundred ninety five (595) nanometers. The annular fixed polarization filter 66P is the same material as the filter 72. The red filter 66F blocks or eliminates any stray light outside of the wavelength range of the LED's 102 which has passed through the sheet material S, thus insuring that only the red light from the LED's 102 reaches the three respective photodetectors 104. Thus, each photodetector 104 generates a signal representative of light intensity of the portion of the reference beam whose polarization angle is aligned with the polarization angle of the fixed polarization filter 66P. The electrical signals from the three respective photodetectors 104-1, 104-2, 104-3 are conducted to the three inputs of the summing amplifier 106 with automatic gain control (AGC) to create a first reference signal $I_\theta$ representative of the polarization angle $\theta$ of the rotating polarization filter 72. The passband filter 62, previously discussed in conjunction with the optics assembly 60, and the red filter 66R each function to eliminate ambient light at wavelengths which would otherwise interfere with generation of the first reference signal.

A second reference signal generator 120 comprises a variable gain amplifier 122 with an associated potentiometer 124, a sample-and-hold circuit 126, and a sheet material presence detector 128. The signal I is presented to the input of the variable gain amplifier 122. The potentiometer 124 controls the gain of the amplifier 122 and thus multiplies the signal I by a factor F to correct for reflection losses from the sheet material. Sheet material presence detector 128 determines the presence of the sheet material in the optical path 20 and asserts the sample and hold circuit 126. In the illustrated example of the first embodiment the sample and hold circuit 126 comprises a combination analog-to-digital-to-analog (A/D/A) convertor circuit.

When the sheet material S is absent from the optical path 20 (as indicated by the presence detector 128) the output of the amplifier 122 is sampled by the sample and hold circuit 126, thereby to generate a second reference signal $F.I_0$ that is representative of the intensity of the beam of unpolarized light from the illuminator, scaled by the reflection loss factor F. the sampled light intensity signal $F.I_0$ is held as long as the sheet is present in the optical path 20.

The sheet material presence detector 128 may be implemented using a manually activated switch 128S. An operator, noting the absence of a sheet material, asserts the switch 128S to generate a command signal to the sample and hold circuit 126. Alternatively, the sheet material presence detector 128 and the command signal output therefrom may implemented automatically. The presence or absence of sheet material S may be determined by the comparison of a signal representative of a detected absorbance characteristic A with a predetermined reference absorbance value $A_r$.

The analysis subsystem 14 is also illustrated in FIG. 3. The analysis subsystem 14 includes an analysis circuit having a logarithmic or log amplifier 142 connected to a low pass filter 144 and a synchronous detector and phase measurement network 146. The analysis circuit is responsive to the light intensity signal $I_s$, the first reference signal $I_\theta$, and the second reference signal $F.I_0$ for generating signals representative of (1) angle of maximum absorbance $\theta_{max}$, (2) specific dichroism ($\Delta A/A$), and (3) absorbance characteristic A.

In operation, the second reference signal $F.I_0$ is presented to a first input 142-1 of the log amplifier 142 while the light intensity signal $I_s$ generated by the photodetector assembly 90 is introduced to a second input 142-2 thereof. The output of the log amplifier 142 is equal to the logarithm of the ratio of the reflection loss corrected signal $F.I_0$ and light intensity signal $I_s$. This output represents the instantaneous absorbance signal A. Thus, $A = \log (F.I_0)/(I_s)$.

The signal from the log amplifier 142 is filtered by the low pass filter 144 to generate a mean, or average, of the absorbance signal A. The synchronous detector and phase measurement network 146 receives the instantaneous absorbance signal A and the first reference signal $I_\theta$. The network 146 extracts from these signals the DC analog signals proportional to ($\Delta A/A$) or Specific Dichroism, and the angle of maximum absorbance $\theta_{max}$. The three signals, Specific Dichroism ($\Delta A/A$), angle of maximum absorbance $\theta_{max}$, and the average absorbance A are each conducted by cables to the control and recording subsystem 16.

The synchronous detector and phase measurement network 146 is disclosed in U.S. Pat. No. 4,521,111 (Paulson, Jr. and Faulhaber), assigned to the assignee of the present invention. This patent is incorporated herein by reference. The angle of maximum absorbance $\theta_{max}$ as used herein is equivalent to the "orientation angle" $\theta$ as discussed in this referenced patent. The parameter Specific Dichroism ($\Delta A/A$), as used herein is mathematically equivalent to the parameter $D_{ex}$ as discussed in this referenced patent.

The control and recording subsystem 16 is also illustrated in FIG. 3. Operation of the optical subsystem 12 and the analysis subsystem 14 are controlled by the control and recording subsystem 16. The subsystem 16 is typically implemented using an IBM PC/AT-compatible personal computer, such as that sold by Everex Corp., Freemont, Calif. as Model 386/33. Accessory modules, installed within the computer subsystem 16, provide control signals to the optical subsystem 12 and receive measurement signals from the analysis subsystem 14. One such accessory module is a combination analog-to-digital converter, input/output (A/D/IO) module 16-1. This module 16-1 receives for recordation the analog inputs representing the measured parameters, Specific Dichroism ($\Delta A/A$), angle of maximum absorbance $\theta_{max}$, and the average absorbance A. This module 16-1 also provides digital control outputs to the subsystem 14. For example, the module 16-1 generates the RESET signal to the network 146 and a control signal to the sample and hold module 126 (when the same is used in an automatic implementation of the sheet material presence detector 128. Preferred for use as the module 16-1 is a device sold by Data Translation Inc., Marlboro, Mass., as Model DT2801.

The Specific Dichroism ($\Delta A/A$), angle of maximum absorbance $\theta_{max}$, and the average absorbance A signals are conducted to respective inputs of a twelve-bit resolution analog-to-digital (A/D) converter, which is part of the preferred implementation of the module 16-1, installed in the computer subsystem 16. The module 16-1 is in communication with the computer data bus 16B. Suitable software allows the central processing unit 16C of computer 16: to acquire digital representations of all three signals as a function of position on the sheet material S; to store the data representing these signals in random access memory (RAM) 16R or on a suitable nonvolatile storage device 16D, such as a disk drive; to create and present plots of the data on a cathode ray tube (CRT) 16T or other plotting device 16P; and to receive commands from the operator through an operator input device such as keyboard 16K. Historical data from previous samples of sheet material, previously stored in RAM or on the nonvolatile storage device, can be recalled and presented for comparison.

A second accessory module is a filter wheel interface module 16-2. This module 16-2, which also communicates with the computer data bus 16B, provides a control signal over the line 88 to the filter wheel assembly 80. This module may be implemented using a device sold by Oriel Corporation as Model 77375, to be used in conjunction with the preferred controller 86 identified above.

In operation, samples of sheet material, typically cut in strips of the desired length and in widths from one inch (1", 2 cm) to two and one-eighth inches (2⅛", 4 cm), are loaded on spools 26S for scanning on the drive unit 26. Transparent film leaders, typically ten (10) inches long and seventy (70) mm wide, three (3) mil thick clear polyethylene terephthalate (PET), are spliced on each end of the sheet material sample with a suitable, optically transparent tape. Scans of each group are started by a manually activating the drive unit 26. Initiation of recordation of measured parameters, the generation of the sheet material presence signal (which asserts the sample-and-hold circuit 126) and the RESET signal to the synchronous detector and phase measurement network 146 are automatically handled by the control and recording subsystem 16. The sample of sheet material is typically transported at a constant calibrated scan speed. The start and end of each sample is determined by the subsystem 16 by detecting the abrupt changes in the absorbance A as the leading and trailing end of each sample crosses the optical path 20.

If desired, any number of samples may be spliced together in an end-to-end manner with a transparent film leader between each sample, up to the capacity of the supply spool 26S-1 on the drive unit 26. Since the appropriate wavelength passband filter 82 must be selected to match the optical absorbance characteristic of the sample being characterized, samples of the same thickness or the optical absorbance are typically grouped together. Samples are cut and mounted with the same orientation as they were manufactured so that plots of the measured optical characteristics may be readily compared.

The sample(s) is(are) threaded from the supply spool 26S-1 and through rollers to the take-up spool 26S-2, all as shown in FIG. 2. Calibration checks are typically made before loading the sample(s). The operator manually controls the drive unit 26 to advance the sample(s) at the desired speed.

The sheet material presence detector switch 128S is manually asserted at the start of each group of measurements to sample and hold the intensity signal with sample absent from the optical path 20. The switch 128S is also asserted each time a wavelength passband filter 82 is changed prior to measurement. The second reference signal ($F.I_0$) is held indefinitely by the sample and hold circuit 126 until the switch 128S is again manually asserted. The switch 128S is activated periodically to correct for changes in intensity of the light source 42, typically at about thirty (30) minute intervals since the source intensity may drift over a period of several hours. The value of the reflection loss correction factor F need only be changed if samples having a different index of refraction are to be characterized.

With the necessary data collection software program loaded in the control and recording subsystem 16, the operator enters a wavelength filter 82 selection and sample information. The filter wheel interface module 16-2 asserts the controller 85 which, in turn, applies a signal over the line 88 to the filter wheel 84 to position a selected filter 82 in the optical path 20. The A/D convertor of the module 16-1 digitizes the signals received from the analysis subsystem 14.

If a group of samples is being characterized, it is preferred that the sheet presence detector switch 128 be asserted automatically by the subsystem 16. Accordingly, the digitized absorbance signal from the A/D converter of the module 16-1 is compared by the processing unit 16C to a predetermined threshold absorbance value, typically corresponding to a absorbance of (0.1). When the leading edge of the optically absorbing sample crosses the optical path 20 the absorbance value A exceeds the threshold level, causing the A/D convertor to begin to measure, at predetermined time intervals (typically 0.25 seconds) the values of specific dichroism ($\Delta A/A$), absorbance A, and angle of maximum absorbance $\theta_{max}$. These measured values are transferred from the module 16-1 via the databus 16B for storage in the memory 16R. A real-time plot of any or all parameter(s), typically the specific dichroism ($\Delta A/A$), is presented on the screen of the computer CRT display device 16T. When the trailing edge of the sample crosses the optical path 20 and the absorbance value A drops below the threshold level, measurements stop and the computer signals the operator that the measurement of the sample is complete.

After the sample is scanned, the plots of the one, some or all of the measured parameters may be presented on the CRT screen and/or plotted on the plotting device along with sample information and statistical data. The data may be stored on the storage device 16D if desired.

The apparatus 10 of a second embodiment of the present invention is particularly adapted for use in an on-line manufacturing environment, includes the traversing transport unit 30.

The optical subsystem 12 of the second embodiment is similar in construction and operates in a similar manner to that of the first embodiment with several minor modifications to better adapt the optical subsystem 12 to the on-line environment, as discussed below. The illuminator 40 is mounted on a first movable carriage 30-1 of transport unit 30 on one side of a moving web of sheet material S while the receiver 50 is mounted on a second movable carriage 30-2 disposed on the opposite side of the moving web S. The illuminator 40 generates a beam of illumination along an optical path 20 which passes through the moving web S to the light receiver 50.

The transport unit 30 is a commercial unit, available from Measurex Corporation of Cupertino, Calif., customized in accordance with Measurex drawing number 2366-2I. In operation, the transport unit 30 causes the first movable carriage to scan across the sheet of light absorbing sheet material S which is moving in a machine direction, the illuminator unit 40 being mounted on the first movable carriage 30-1 to be transported in a transverse direction transverse to the machine direction and the receiver unit 50 being mounted on a second movable carriage 30-2 to be transported in registration with the illuminator unit 40. In other words the illuminator 40 and the light receiver 50 remain in optical alignment with each other at all times.

The transport unit 30 has an internal control unit 32 which generates a motion signal 32M indicating movement of the movable carriages and the optical subsystem 12; a direction indicator signal 32D indicating the direction of carriage motion (forward and reverse); and a motion increments signal 32I indicating each increment of motion of the carriages. Passage of the carriages past a switch (not shown) located in the transport unit 30 generates a "center of web" signal 32C indicating that the optical subsystem 12 is located at the approximate center of the web S. The signals 32M, 32D, 32I and 32C are transmitted from the internal control unit 32 of the transport unit 30 to the control and recording subsystem 16 via a cable and are received by computer module 16-1 so that the position of the optical subsystem 12 relative to the web S may be tracked. The signals 32M, 32D, 32I, 32C cooperate with the subsystem 16 to provide a carriage position sensor for sensing the transverse position of the movable carriages 30-1 and 30-2 of the transport unit 30 relative to the moving sheet material S and means for generating a signal representative of carriage position. The subsystem 16, under control of appropriate software, thus implements the function of a carriage position sensor which receives the motion encoder signal 32M and direction of motion signal 32D generates a parameter which represents the transverse position of the illuminator and light receiver relative to the moving sheet material.

The illuminator 40 of the second embodiment produces a collimated beam, rather than a focused beam, of unpolarized light which is passed through the sheet material S. As may be seen in FIG. 5, the second focussing lens 48 is omitted in the illuminator 40 of the second embodiment. The illuminator 40 in the second embodiment thus comprises a source of unpolarized light and collimating means for receiving light from the source and forming a collimated beam.

Due to space constraints of the on-line environment, the first focussing lens 61 in the light receiver 50 typically has a somewhat shorter focal length than its counterpart in the light receiver of the first embodiment. Thus, a twenty-five (25) millimeter focal length Model KBX046 lens may be used.

Mechanical vibrations from manufacturing machinery can present problems in an on-line environment. The use of a collimated light beam minimizes the effects of vibration-related lateral displacements between the illuminator 40 and the light receiver 50 which may occur while, the transport unit 30 is in motion. To further reduce the size of the light receiver 50 shorter focal length lenses, such as a thirty-eight (38) millimeter focal length Model KPX079 lenses may be used instead of the fifty (50) millimeter focal length lenses of the first embodiment.

In this embodiment the subsystem 16 records the parameter representative of carriage position and, simultaneously, the signals from the receiver 50 representative of the measured parameters (i.e., specific dichroism, angle of maximum absorbance, and absorbance).

Since the second embodiment is adapted to the on-line manufacturing environment, characterization of polarization dependent properties of entire rolls of a light absorbing sheet material, such as polymeric film, is desired. Typically the transport unit 30 continuously scans the optical subsystem 12 transversely across the web S from one lateral edge to the other. On each pass across the web S the transport unit 30 transports the carriages such that the optical path 20 of the optical subsystem 12 moves beyond each lateral edge of the web S. Passage of the optical path 20 past the lateral edge of the web S is detected by the subsystem 16 when an abrupt change in absorbance A occurs. The signal analysis subsystem 14 continuously measures the polarization dependent properties of the web S. At predetermined intervals across the web these measurements are converted to digital values by the A/D converter of the module 16-1 and stored in the memory 16R. By comparing consecutive absorbance A values with a predetermined reference value $A_r$, the presence of the sheet material in the optical path is determined. The subsystem 16 implements sheet presence detector means to determine when the position of the optical path 20 is between a first and a second lateral edge of the sheet material. A data file may be collected for each roll of material produced and a statistical summary of the measured parameters may be calculated therefor.

Polymeric film is typically manufactured in a continuous manner and typically wound into rolls. Typically, at the beginning of a new roll of sheet material a new data file is opened, and the subsystem 16 waits until a reverse direction scan of the transport unit 30 occurs. When the "center of film" signal 32C is generated, a software "transverse position" counter is loaded with a count value corresponding to one-half the width of the sheet. Carriage motion increment pulses 321 are divided by a predetermined value to produce a pulse for each measurement increment (typically 0.10 inch) of carriage travel. For each measurement increment the transverse position counter is decremented and an absorbance measurement is made, converted to a digital value by the module 16-1, and compared to a threshold value to determine when the optical path 20 has passed a lateral edge of the sheet.

After the edge of the sheet is detected and the signal 32M indicates that carriage motion is stopped, the sample and hold circuit 120 is asserted to generate the second reference signal $F.I_0$. This sequence insures that the $F.I_0$ signal is properly calibrated, with no film in the optical path, prior to each scan of the optical subsystem 12 across the web.

If desired, a system calibration curve of the $F.I_0$ signal may be generated with the sheet material absent from the optical path. The $F.I_0$ signal may be recorded as the carriage moves across the film to correct for any minor variations in system performance that might be related to carriage position.

As the optical subsystem 12 moves across the film, the parameters of specific dichroism ($\Delta A/A$), absorbance A, and angle of maximum absorbance $\theta_{max}$ are converted to digital values by module 16-1 at predetermined recording intervals, typically one-half (0.5) inch, and the digital values are stored by the subsystem 16. Each measured value of absorbance is compared to the threshold value to detect the passage of the optical path 20 past the second lateral edge of the web S. When this occurs the last set of measured values is discarded and the measurement stops.

Those skilled in the art, having the benefit of the teachings of the present invention as hereinabove set forth, can effect numerous modifications thereto. It is readily appreciated that such modifications can be made without departing from the spirit of the scope of the; present invention. Accordingly, such modifications are to be construed as being encompassed within the scope of the present invention as set forth in the appended claims.

What is claimed is:

1. An apparatus for detecting polarization dependent properties of a light absorbing sheet material having an absorbance characteristic A, an absorbance variation due to polarization $\Delta A$, and a reflection loss factor F, the apparatus comprising:

an illuminator for illuminating a sheet of light absorbing sheet material with a beam of unpolarized light;
a light receiver including a rotating polarization filter for receiving light transmitted through the sheet and for generating a sinusoidally varying light intensity signal $I_s$ representative of the intensity of polarized light in a predetermined range of wavelengths, the illuminator and the receiver defining an optical path,
wherein the light receiver comprises in optical sequence:
a first focussing lens for focussing the received light to a first focal point,
a first collimating lens for forming a first collimated beam,
a rotating linear polarization filter positioned to receive the first collimated beam and to pass therethrough only a portion of the light in the first collimated beam whose polarization angle is aligned with the polarization angle of the filter,
a second focussing lens for focussing the first collimated beam to a second focal point,
a second collimating lens for forming a second collimated beam, a wavelength passband filter positioned to receive the second collimated beam and pass therethrough only a predetermined range of wavelengths, a third focussing lens for focussing the second collimated beam to a third focal point, a photodetector at the third focal point for generating the light intensity signal $I_s$;

the light intensity signal $I_s$ having a minimum value $I_{s\ min}$ at a first polarization angle of maximum absorbance $\theta_{max}$ and a maximum value $I_{s\ max}$ at a second polarization angle of minimum absorbance $\theta_{min}$;

a first reference signal generator for generating a first reference signal $I_\theta$ representative of the polarization angle $\theta$ of the rotating polarization filter;

a second reference signal generator for generating a second reference signal $F \cdot I_0$ representative of the intensity of the beam of unpolarized light from the illuminator scaled by the reflection loss factor $F$;

an analysis circuit responsive to the light intensity signal $I_s$, the first reference signal $I_\theta$, and the second reference signal $F \cdot I_0$ for generating signals representative of the angle of maximum absorbance $\theta_{max}$,
the specific dichroism ($\Delta A/A$), and
the absorbance characteristic $A$, where the specific dichroism ($\Delta A/A$) is defined as $$(\Delta A/A) = \frac{\log I_{s\ min} - \log I_{s\ max}}{\log F \cdot I_0 - \tfrac{1}{2}\log I_{s\ min} - \tfrac{1}{2}\log I_{s\ max}}$$

and where
the absorbance characteristic $A$ is defined as $$A = \log F \cdot I_0 \tfrac{1}{2}\log I_{s\ min} \tfrac{1}{2}\log I_{s\ max}.$$

2. The apparatus of claim 1 wherein the illuminator illuminates the sheet with the beam of unpolarized light, the beam of light being focussed on the sheet, the illuminator comprising;
   a source of unpolarized light, and
   focussing means for receiving light from the source and forming a beam focussed to a focal point on the sheet.

3. The apparatus of claim 1, wherein the illuminator illuminates the shet with the beam of unpolarized light, the beam of light being collimated, the illuminator comprising:
   a source of unpolarized light, and
   collimating means for receiving light from the source and forming a collimated beam.

4. The apparatus of claim 1 wherein the second reference signal generator comprises:
   a sheet presence detector to determine the presence of the sheet in the optical path;
   a sample and hold circuit responsive to the sheet presence detector for sampling the light intensity signal $I_s$ to generate the second reference signal $F \cdot I_0$ when the sheet is absent from the optical path and for holding the sampled light intensity signal as long as the sheet is present in the optical path.

5. The apparatus of claim 4 wherein the sheet presence detector comprises a manually activated switch.

6. The apparatus of claim 4 wherein the sheet presence detector comprises:
   means for comparing the the absorbance characteristic $A$ with a predetermined reference absorbance value to determine the presence of the sheet in the optical path.

7. The apparatus of claim 1 further comprising:
   a transport unit for scanning a first movable carriage across the sheet of light absorbing sheet material which is moving in a machine direction, the illuminator being mounted on the first movable carriage to be transported in a direction transverse to the machine direction;
   a second movable carriage for transporting the light receiver across the moving sheet in registration with the illuminator.

8. The apparatus of claim 7, further comprising:
   a carriage position sensor for sensing the transverse position of the movable carriages of the transport unit relative to the moving sheet material and for generating a signal representative thereof;
   recording means for simultaneously receiving and recording the signals representative of the specific dichroism, the angle of maximum absorbance, the average absorbance of the sheet, and the carriage position.

9. The apparatus of claim 8 wherein the carriage position sensor comprises:
   a motion encoder which generates, a signal indicating increments of motion of the movable carriages;
   a direction indicator which generates a signal indicating the direction of motion of the movable carriages; and
   a bidirectional counter which receives the motion encoder signal and direction indicator signal and whose output signal represents the transverse position of the illuminator and the light receiver relative to the moving sheet material.

10. The apparatus of claim 7 wherein the second reference signal generator comprises:
    a sheet presence detector to determine the presence of the sheet in the optical path by determining when the position of the optical path is between a first lateral edge and a second lateral edge of the sheet;
    a sample and hold circuit responsive to the sheet presence detector for sampling the light intensity signal $I_s$ to generate the second reference signal $F \cdot I_0$ when the sheet is absent from the optical path and for holding the sampled light intensity signal as long as the sheet is present in the optical path.

11. The apparatus of claim 1 wherein the analysis circuit comprises:
    a logarithmic amplifier responsive to the light intensity signal $I_s$ and the second reference signal $F \cdot I_0$ to generate a time-varying absorbance signal having a direct component and an alternating component, the time-varying signal representing the logarithm of the signal $F \cdot I_0$ divided by the signal $I_s$;
    a synchronous detector and phase measurement circuit to generate the specific dichroism ($\Delta A/A$), where the quantity ($\log I_{s\ min} - \log I_{s\ max}$) is the alternating component of the time-varying absorbance signal and the quantity ($\log F \cdot I_0 - \tfrac{1}{2}\log I_{s\ min} - \tfrac{1}{2}\log I_{s\ max}$) is the direct component of the time-varying absorbance signal; and
    the angle of maximum absorbance $\theta_{max}$ corresponding to the maximum value of the time-varying absorbance signal.

12. An apparatus for detecting polarization dependent properties of a light absorbing sheet material having an absorbance characteristic $A$, an absorbance variation due to polarization ΔA, and a reflection loss factor F, the apparatus comprising:

an illuminator for illuminating a sheet of light absorbing sheet material with a beam of unpolarized light;

a light receiver including a rotating polarization filter for receiving light transmitted through the sheet and for generating a sinusoidally varying light intensity signal $I_s$ representative of the intensity of polarized light in a predetermined range of wavelengths, the illuminator and the receiver defining an optical path, wherein the light receiver comprises in optical sequence:

a first focussing lens for focussing the received light to a first focal point, a first collimating lens for forming a first collimated beam, a rotating linear polarization filter positioned to receive the first collimated beam and to pass therethrough only a portion of the light in the first collimated beam whose polarization angle is aligned with the polarization angle of the filter, a second focussing lens for focussing the first collimated beam to a second focal point, a second collimating lens for forming a second collimated beam, a wavelength passband filter positioned to receive the second collimated beam and pass therethrough only a predetermined range of wavelengths, a third focussing lens for focussing the second collimated beam to a third focal point, a photodetector at the third focal point for generating the light intensity signal $I_s$;

the light intensity signal $I_s$ having a minimum value $I_{s\ min}$ at a first polarization angle of maximum absorbance $\theta_{max}$ and a maximum value $I_{s\ max}$ at a second polarization angle of minimum absorbance $\theta_{min}$;

a first reference signal generator for generating a first reference signal $I_\theta$ representative of the polarization angle $\theta$ of the rotating polarization filter;

a second reference signal generator for generating a second reference signal $F.I_0$ representative of the intensity of the beam of unpolarized light from the illuminator scaled by the reflection loss factor F;

an analysis circuit responsive to the light intensity signal $I_s$, the first reference signal $I_\theta$, and the second reference, signal $F.I_0$ for generating signals representative of the angle of maximum absorbance $\theta_{max}$, the specific dichroism (ΔA/A), and
the absorbance characteristic A, where the specific dichroism (ΔA/A) is defined as $$(\Delta A/A) = \frac{\log I_{s\ min} - \log I_{s\ max}}{\log F \cdot I_0 - \tfrac{1}{2}\log I_{s\ min} - \tfrac{1}{2}\log I_{s\ max}}$$

and where
the absorbance characteristic A is defined as $$A = \log F.I_0 - \tfrac{1}{2}\log I_{s\ min} - \tfrac{1}{2}\log I_{s\ max}$$

wherein the first reference signal generator comprises:

a circular array of light emitting diodes for generating a plurality of reference beams, the array being symmetrically disposed about the first focal point;

an annular fixed polarization filter positioned adjacent the second focal point;

a circular array of photodetectors symmetrically disposed about the second focal point immediately behind the fixed polarization filter;

a summing amplifier having a plurality of inputs, each input being connected to a respective one of the photodetectors;

wherein:

each reference beam from each light emitting diode is collimated by the first collimating lens;

each collimated reference beam passes through the rotating polarization filter;

each collimated reference beam is focussed by the second focussing lens onto a respective photodetector, each focussed reference beam having passed through the fixed polarization filter prior to the respective photodetector;

each photodetector generates a signal representative of light intensity of the portion of the reference beam whose polarization angle is aligned with the polarization angle of the fixed polarization filter; and the signals from the photodetectors are conducted to the summing amplifier whose output generates the first reference signal $I_\theta$ representative of the polarization angle $\theta$ of the rotating polarization filter.

13. The apparatus of claim 12 wherein the first reference signal generator further comprises at least one passband filter to eliminate ambient light at wavelengths which interfere with generation of the first reference signal.

* * * * *